United States Patent
He et al.

(10) Patent No.: US 10,633,970 B2
(45) Date of Patent: Apr. 28, 2020

(54) DRILLING FLUID CONTAMINATION DETERMINATION FOR DOWNHOLE FLUID SAMPLING TOOL

(71) Applicant: Halliburton Energy Services, Inc., Houston, TX (US)

(72) Inventors: Tian He, Houston, TX (US); Mehdi Alipour Kallehbasti, Kingwood, TX (US); Ming Gu, Humble, TX (US); Christopher Michael Jones, Houston, TX (US); Darren Gascooke, Houston, TX (US); Michael T. Pelletier, Houston, TX (US); Di Du, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/546,972

(22) PCT Filed: Aug. 11, 2016

(86) PCT No.: PCT/US2016/046602
§ 371 (c)(1),
(2) Date: Jul. 27, 2017

(87) PCT Pub. No.: WO2018/031021
PCT Pub. Date: Feb. 15, 2018

(65) Prior Publication Data
US 2019/0100995 A1    Apr. 4, 2019

(51) Int. Cl.
*E21B 49/08*    (2006.01)
*G01N 1/10*    (2006.01)
(Continued)

(52) U.S. Cl.
CPC ...... *E21B 49/081* (2013.01); *E21B 2049/085* (2013.01); *G01N 1/10* (2013.01); *G01N 33/241* (2013.01); *G06F 17/11* (2013.01)

(58) Field of Classification Search
CPC ............ E21B 2049/085; E21B 49/081; G01N 33/241; G06F 17/11
See application file for complete search history.

(56) References Cited

U.S. PATENT DOCUMENTS 7,081,615 B2 * 7/2006 Betancourt ............. E21B 47/10
250/255
7,526,953 B2    5/2009 Goodwin et al.
(Continued)

FOREIGN PATENT DOCUMENTS

GB    2445043 A *   6/2008 ............. E21B 47/10
WO    2010071619      6/2010
(Continued)

OTHER PUBLICATIONS

International Search Report and Written Opinion for Application No. PCT/US2016/046602 dated May 1, 2017.
(Continued)

*Primary Examiner* — John Fitzgerald
(74) *Attorney, Agent, or Firm* — Benjamin Fite; C. Tumey Law Group PLLC

(57) ABSTRACT

Disclosed are methods and systems for determination of fluid contamination of a fluid sample from a downhole fluid sampling tool. A method may comprise obtaining a fluid sample, obtaining input parameters, wherein the input parameters comprise fluid properties obtained from measurement of the fluid sample and mud filtrate composition, obtaining initial values of iterative parameters, determining component mole fractions of the reservoir fluid using the initial values of the iterative parameters in a mole fraction distribution function, determining calculated fluid properties
(Continued)

of the reservoir fluid using equation of state flash calculating, and repeating steps of determining component mole fractions and determining calculated fluid properties and further obtaining updated values of the iterative parameters for use in the mole fraction distribution function until a comparison of one or more of the calculated fluid properties with one or more of the input parameters is within a tolerance error.

15 Claims, 10 Drawing Sheets

(51) Int. Cl.
 *G01N 33/24* (2006.01)
 *G06F 17/11* (2006.01)

(56) References Cited

U.S. PATENT DOCUMENTS

| | | | | |
|---|---|---|---|---|
| 7,920,970 | B2* | 4/2011 | Zuo | G01N 33/2823 |
| | | | | 702/11 |
| 8,805,617 | B2* | 8/2014 | Zuo | E21B 49/10 |
| | | | | 702/11 |
| 8,996,346 | B2* | 3/2015 | Zuo | E21B 47/10 |
| | | | | 703/10 |
| 9,255,475 | B2* | 2/2016 | Zuo | E21B 49/10 |
| 9,557,312 | B2* | 1/2017 | Zuo | G01N 33/2841 |
| 9,612,361 | B2 | 4/2017 | Chen et al. | |
| 9,934,367 | B2* | 4/2018 | Chen | G01N 33/2823 |
| 10,294,785 | B2* | 5/2019 | Wang | E21B 49/10 |
| 10,295,522 | B2* | 5/2019 | Zuo | G01N 33/2841 |
| 2004/0104341 | A1* | 6/2004 | Betancourt | E21B 47/10 |
| | | | | 250/255 |
| 2006/0226699 | A1* | 10/2006 | Betancourt | E21B 47/10 |
| | | | | 303/113.2 |
| 2011/0088949 | A1 | 4/2011 | Zou et al. | |
| 2011/0284219 | A1 | 11/2011 | Pomerantz et al. | |
| 2012/0296617 | A1 | 11/2012 | Zuo et al. | |
| 2014/0316705 | A1 | 10/2014 | Zou et al. | |
| 2015/0167456 | A1 | 6/2015 | Irani | |
| 2015/0184510 | A1 | 7/2015 | Gao et al. | |
| 2016/0161462 | A1* | 6/2016 | Iyer | E21B 47/06 |
| 2016/0369600 | A1* | 12/2016 | Wong | E21B 41/0092 |
| 2016/0369605 | A1* | 12/2016 | Wong | E21B 43/12 |
| 2017/0009558 | A1* | 1/2017 | Wong | E21B 43/00 |
| 2017/0091359 | A1* | 3/2017 | Wong | E21B 43/14 |
| 2019/0017377 | A1* | 1/2019 | He | E21B 49/081 |

FOREIGN PATENT DOCUMENTS

| | | | | |
|---|---|---|---|---|
| WO | | 2012094007 | 7/2012 | |
| WO | | 2015134043 | 9/2015 | |
| WO | | 2015138805 | 9/2015 | |
| WO | | 2017086949 | 11/2015 | |
| WO | WO-2018231252 A1 * | 12/2018 | | E21B 49/08 |

OTHER PUBLICATIONS

Applications of Equations of State in the Oil and Gas Industry, Thermodynamics—Kinetics of Dynamic Systems by Ashour et al dated Sep. 22, 2011.
Extended European Search Report for Application No. 16912837.8 dated Jan. 23, 2020.
Jones, C. M., Van Zuilekom, T., & Iskander, F. "How Accurate Is Enhanced Optical Fluid Analysis Compared to Lab PVT Measurements?" SPWLA 57th Annual Logging Symposium. Jun. 25, 2016. Society of Petrophysicists and Well-Log Analysts. Reykjavik, Iceland.

* cited by examiner

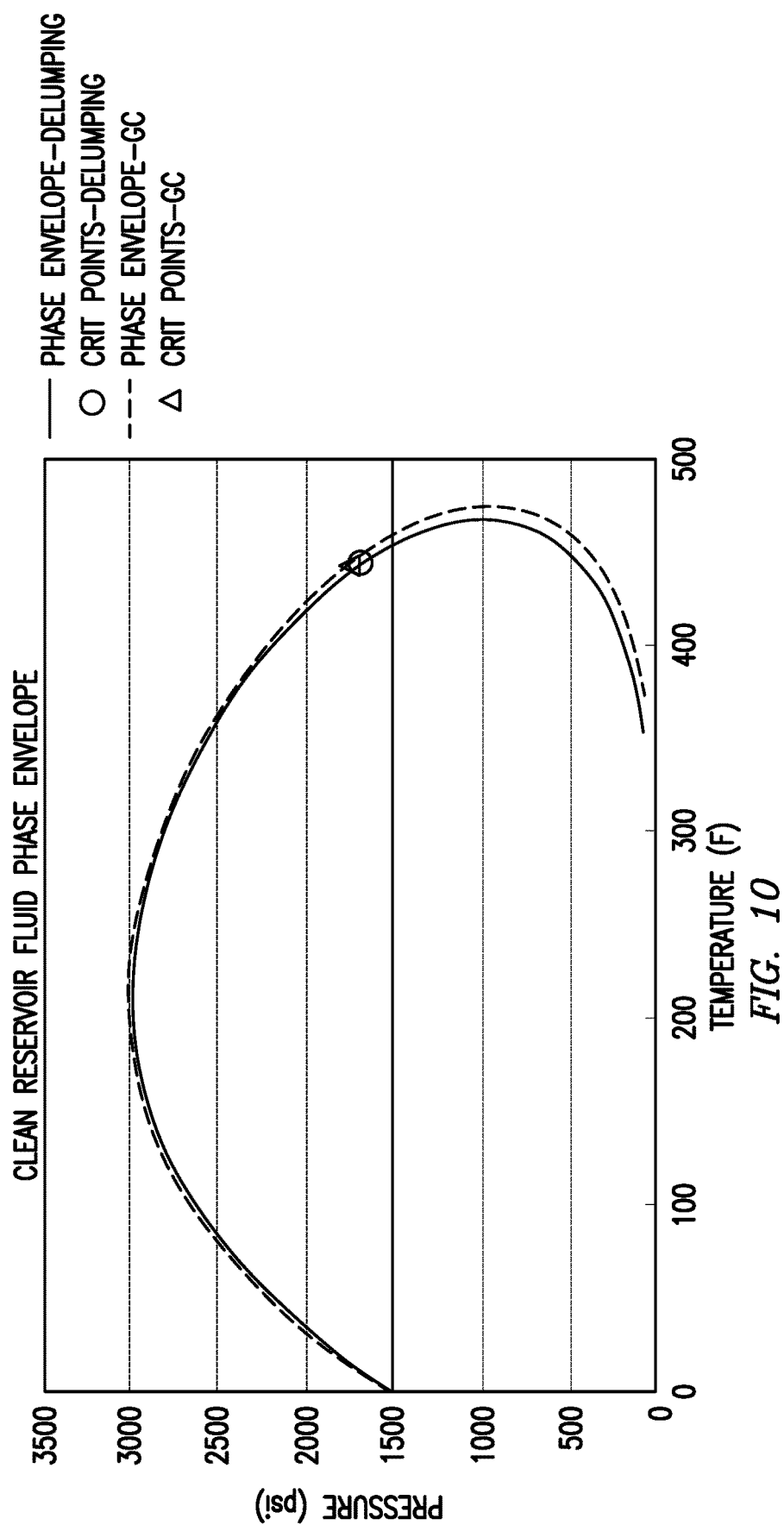

DRILLING FLUID CONTAMINATION DETERMINATION FOR DOWNHOLE FLUID SAMPLING TOOL

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation. One technique for collecting relevant information involves obtaining and analyzing fluid samples from a reservoir of interest. There are a variety of different tools that may be used to obtain the fluid sample. The fluid sample may then be analyzed to determine fluid properties, including, without limitation, component concentrations, plus fraction molecular weight, gas-oil ratios, bubble point, dew point, phase envelope, viscosity, combinations thereof, or the like. Conventional analysis has required transfer of the fluid samples to a laboratory for analysis. Downhole analysis of the fluid sample may also be used to provide real-time fluid properties, thus avoiding delays associated with laboratory analysis.

Accurate determination of fluid properties may be problematic as the fluid sample may often be contaminated with drilling fluids. Fluid samples with levels of drilling fluid contamination may result in non-representative fluids and measured properties. Techniques to determine drilling fluid contamination may include use of pump-out curves, such as density, gas-to-oil ratio and resistivity, among other properties of the fluids. However, determination of drilling fluid contamination using these techniques may be limited, for example, due to lack of significant decrease of the property value, non-linear behavior or properties to contamination levels, and unreliable property measurements. To reduce drilling fluid contamination, longer pump-out time may be required, which can lead to loss of rig time and increase risk of stuck tools, among other problems.

BRIEF DESCRIPTION OF THE DRAWINGS

These drawings illustrate certain aspects of some of the embodiments of the present invention, and should not be used to limit or define the invention.

FIG. 10 is a comparison of phase envelopes predicted from predicted and gas chromatograph mole fraction distributions for a clean reservoir fluid.

DETAILED DESCRIPTION

Disclosed herein are methods and systems for determination of contamination level of a fluid sample from a downhole fluid sampling tool. Knowledge of the fluid contamination (e.g., oil based drilling fluid contamination) may then allow right time of sampling and determination of fluid properties of the reservoir fluid, even though the fluid sample was contaminated with well fluid, such as a drilling fluid or other well fluid introduced from the surface. For example, the methods and systems may include a determination of the component concentrations of the reservoir fluid, which may be delumped concentration that includes plus fractions (e.g., C6+) that may ordinarily be lumped together. By way of further example, the methods and systems may further include generation of pressure-volume-temperature properties (e.g., bubble point, phase envelop prediction, etc.) of the reservoir fluid. As will be discussed in more detail below, the methods and systems for fluid characterization may use a distribution function in conjunction with an equation of state to determine fluid contamination and component concentrations of the reservoir fluid, among others. Inputs may include downhole measurements of the fluid sample, including, without limitation, C1, C2, C3, C45 weight percent, gas-oil ratio, oil density (e.g., live oil or dead oil density), and/or bubble point. Inputs may further include a mud filtrate composition.

Figure 1:
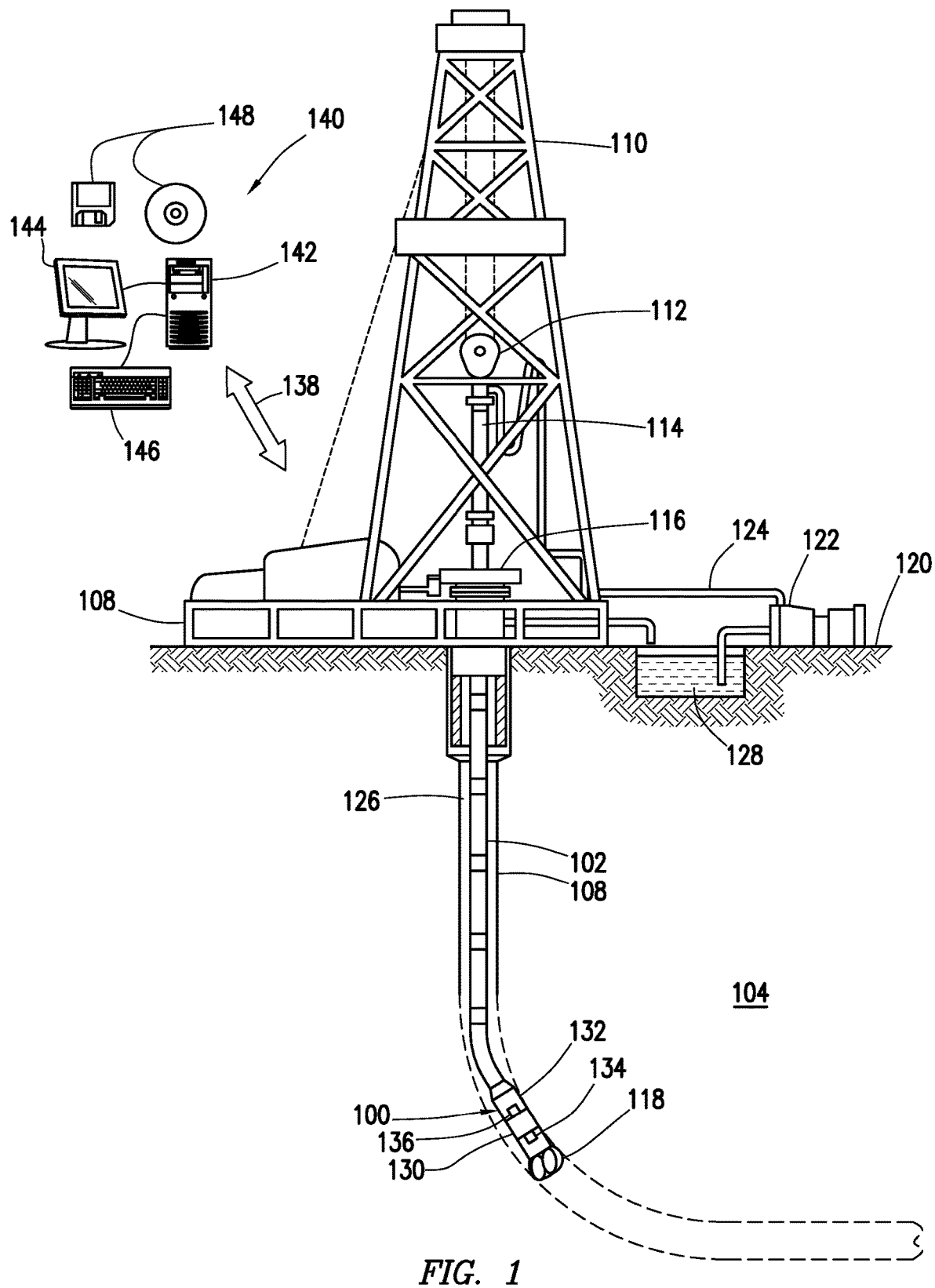
FIG. 1 is a schematic diagram of an example downhole fluid sampling tool on a drill string.

FIG. 1 is a schematic diagram is shown of downhole fluid sampling tool 100 disposed on a drill string 102. The downhole fluid sampling tool 100 may be used to obtain a fluid sample, for example, a fluid sample of a reservoir fluid from subterranean formation 104. The reservoir fluid may be contaminated with well fluid (e.g., drilling fluid) from wellbore 106. As described herein, the fluid sample may be analyzed to determine fluid contamination and other fluid properties of the reservoir fluid. As illustrated, a wellbore 106 may extend through subterranean formation 104. While the wellbore 106 is shown extending generally vertically into the subterranean formation 104, the principles described herein are also applicable to wellbores that extend at an angle through the subterranean formation 104, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 108 may support a derrick 110 having a traveling block 112 for raising and lowering drill string 102. Drill string 102 may include, but is not limited to, drill pipe and coiled tubing, as generally known to those skilled in the art. A kelly 114 may support drill string 102 as it may be lowered through a rotary table 116. A drill bit 118 may be attached to the distal end of drill string 102 and may be driven either by a downhole motor and/or via rotation of drill string 102 from the surface 120. Without limitation, drill bit 118 may include, roller cone bits, PDC bits, natural diamond bits, any hole openers, reamers, coring bits, and the like. As drill bit 118 rotates, it may create and extend wellbore 106 that penetrates various subterranean formations 104. A pump 122 may circulate drilling fluid through a feed pipe 124 to kelly 114, downhole through interior of drill string 102, through orifices in drill bit 118, back to surface 120 via annulus 126 surrounding drill string 102, and into a retention pit 128.

Drill bit 118 may be just one piece of a downhole assembly that may include one or more drill collars 130 and downhole fluid sampling tool 100. Downhole fluid sampling tool 100, which may be built into the drill collars 130 may gather measurements and fluid samples as described herein. One or more of the drill collars 130 may form a tool body 132, which may be elongated as shown on FIG. 1. Tool body 132 may be any suitable material, including without limitation titanium, stainless steel, alloys, plastic, combinations thereof, and the like. Downhole fluid sampling tool 100 may further include one or more sensors 134 for measuring properties of the fluid sample, reservoir fluid, wellbore 106, subterranean formation 104, or the like. The downhole fluid sampling tool 100 may be used to collect a fluid sample from subterranean formation 104. As previously described, the fluid sample may comprise a reservoir fluid, which may be contaminated with a well fluid. The downhole fluid sampling tool 100 may obtain and separately store different fluid samples from subterranean formation 104. However, storing of the fluid samples in the downhole fluid sampling tool 100 may be based on the determination of the fluid contamination. For example, if the fluid contamination exceeds a tolerance, then the fluid sample may not be stored. If the fluid contamination is within a tolerance, then the fluid sample may be stored in the downhole fluid sampling tool 100.

The downhole fluid sampling tool 100 may further include a fluid analysis module 136. The fluid analysis module 136 may be operable to derive properties and characterize the fluid sample. By way of example, the fluid analysis module 136 may measure absorption spectra and translate such measurements into component concentrations of the fluid sample, which may be lumped component concentrations, as described above. The fluid analysis module 136 may also measure gas-to-oil ratio, live fluid density, live fluid viscosity, formation pressure, and formation temperature. The fluid analysis module 136 may also be operable to determine fluid contamination of the fluid sample. The fluid analysis module 136 include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 136 may include random access memory (RAM), one or more processing units, such as a central processing unit (CPU), or hardware or software control logic, ROM, and/or other types of nonvolatile memory.

Any suitable technique may be used for transmitting signals from the downhole fluid sampling tool 100 to the surface 120. As illustrated, a communication link 138 (which may be wired or wireless, for example) may be provided that may transmit data from downhole fluid sampling tool 100 to an information handling system 140 at surface 120. Information handling system 140 may include a processing unit 142, a monitor 144, an input device 146 (e.g., keyboard, mouse, etc.), and/or computer media 148 (e.g., optical disks, magnetic disks) that can store code representative of the methods described herein. The information handling system 140 may act as a data acquisition system and possibly a data processing system that analyzes information from downhole fluid sampling tool 100. For example, information handling system 140 may process the information from downhole fluid sampling tool 100 for determination of fluid contamination. The information handling system 140 may also determine additional properties of the fluid sample (or reservoir fluid), such as component concentrations, pressure-volume-temperature properties (e.g., bubble point, phase envelop prediction, etc.) based on the fluid characterization. This processing may occur at surface 120 in real-time. Alternatively, the processing may occur at surface 120 or another location after recovery of downhole fluid sampling tool 100 from wellbore 106. Alternatively, the processing may be performed by an information handling system in wellbore 106, such as fluid analysis module 136. The resultant fluid contamination and fluid properties may then be transmitted to surface 120, for example, in real-time.

Figure 2:
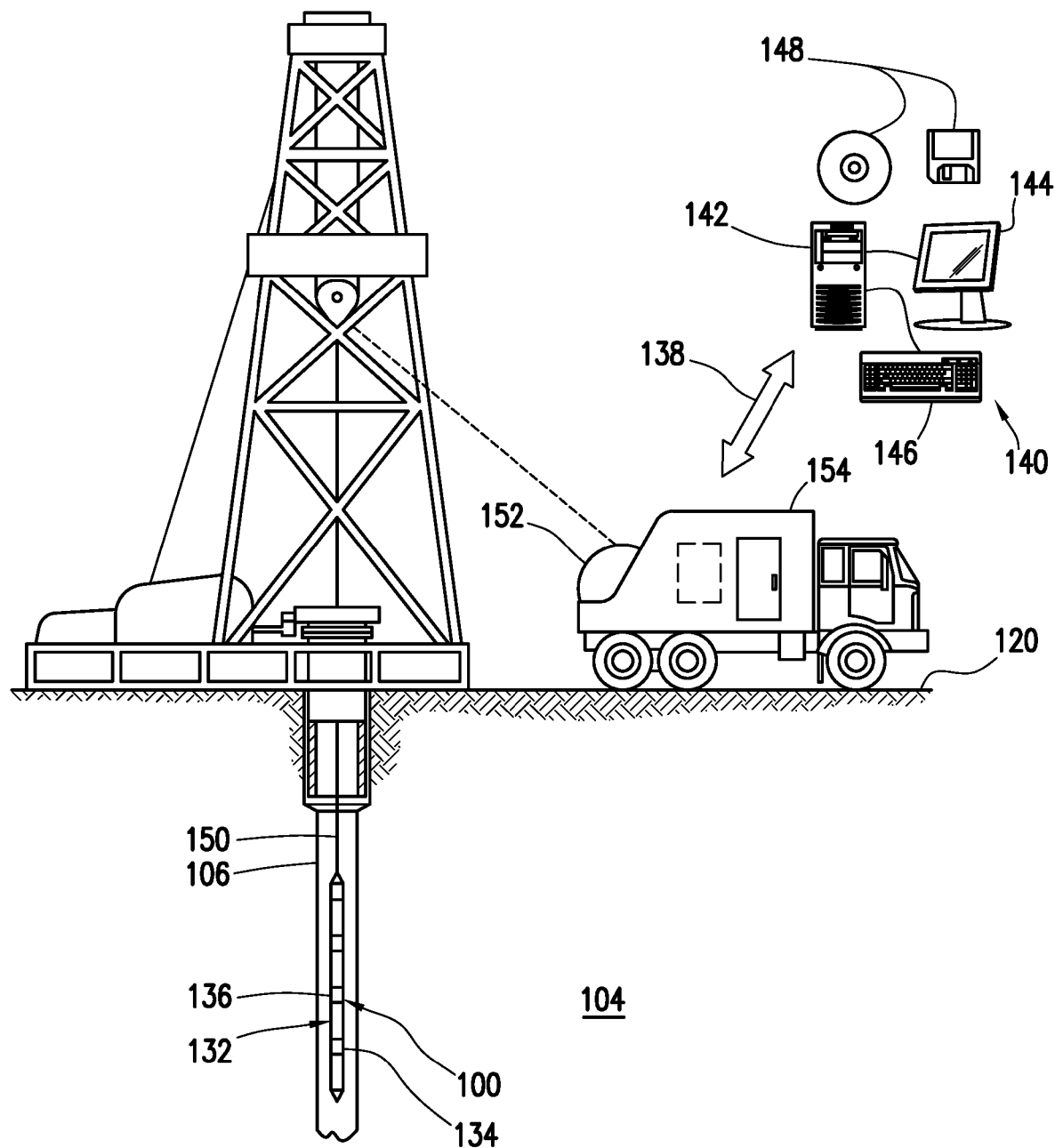
FIG. 2 is a schematic diagram of an example downhole fluid sampling tool on a wireline.

Referring now to FIG. 2, a schematic diagram is shown of downhole fluid sampling tool 100 on a wireline 150. As illustrated, wellbore 106 may extend through subterranean formation 104. Downhole fluid sampling tool 100 may be similar in configuration and operation to downhole fluid sampling tool 100 shown on FIG. 1 except that FIG. 2 shows downhole fluid sampling tool 100 disposed on wireline 150. It should be noted that while FIG. 2 generally depicts a land-based drilling system, those skilled in the art will readily recognize that the principles described herein are equally applicable to subsea drilling operations that employ floating or sea-based platforms and rigs, without departing from the scope of the disclosure.

As illustrated, a hoist 152 may be used to run downhole fluid sampling tool 100 into wellbore 106. Hoist 152 may be disposed on a recovery vehicle 154. Hoist 152 may be used, for example, to raise and lower wireline 150 in wellbore 106. While hoist 152 is shown on recovery vehicle 154, it should be understood that wireline 150 may alternatively be disposed from a hoist 152 that is installed at surface 120 instead of being located on recovery vehicle 154. Downhole fluid sampling tool 100 may be suspended in wellbore 106 on wireline 150. Other conveyance types may be used for conveying downhole fluid sampling tool 100 into wellbore 106, including coiled tubing and wired drill pipe, for example. Downhole fluid sampling tool 100 may comprise a tool body 132, which may be elongated as shown on FIG. 1. Tool body 132 may be any suitable material, including without limitation titanium, stainless steel, alloys, plastic, combinations thereof, and the like. Downhole fluid sampling tool 100 may further include one or more sensors 134 for measuring properties of the fluid sample, reservoir fluid, wellbore 106, subterranean formation 104, or the like. The downhole fluid sampling tool 100 may also include a fluid analysis module 136, which may be operable to process information regarding fluid sample, as described above with respect to FIG. 1. The downhole fluid sampling tool 100 may be used to collect fluid samples from subterranean formation 104. The downhole fluid sampling tool 100 may obtain and separately store different fluid samples from subterranean formation 104.

As previously described, information from downhole fluid sampling tool 100 may be transmitted to an information handling system 140, which may be located at surface 120.

As illustrated, communication link 138 (which may be wired or wireless, for example) may be provided that may transmit data from downhole fluid sampling tool 100 to an information handling system 140 at surface 120. Information handling system 140 may include a processing unit 142, a monitor 144, an input device 146 (e.g., keyboard, mouse, etc.), and/or computer media 148 (e.g., optical disks, magnetic disks) that can store code representative of the methods described herein. In addition to, or in place of processing at surface 120, processing may occur downhole (e.g., fluid analysis module 136).

Figure 3:
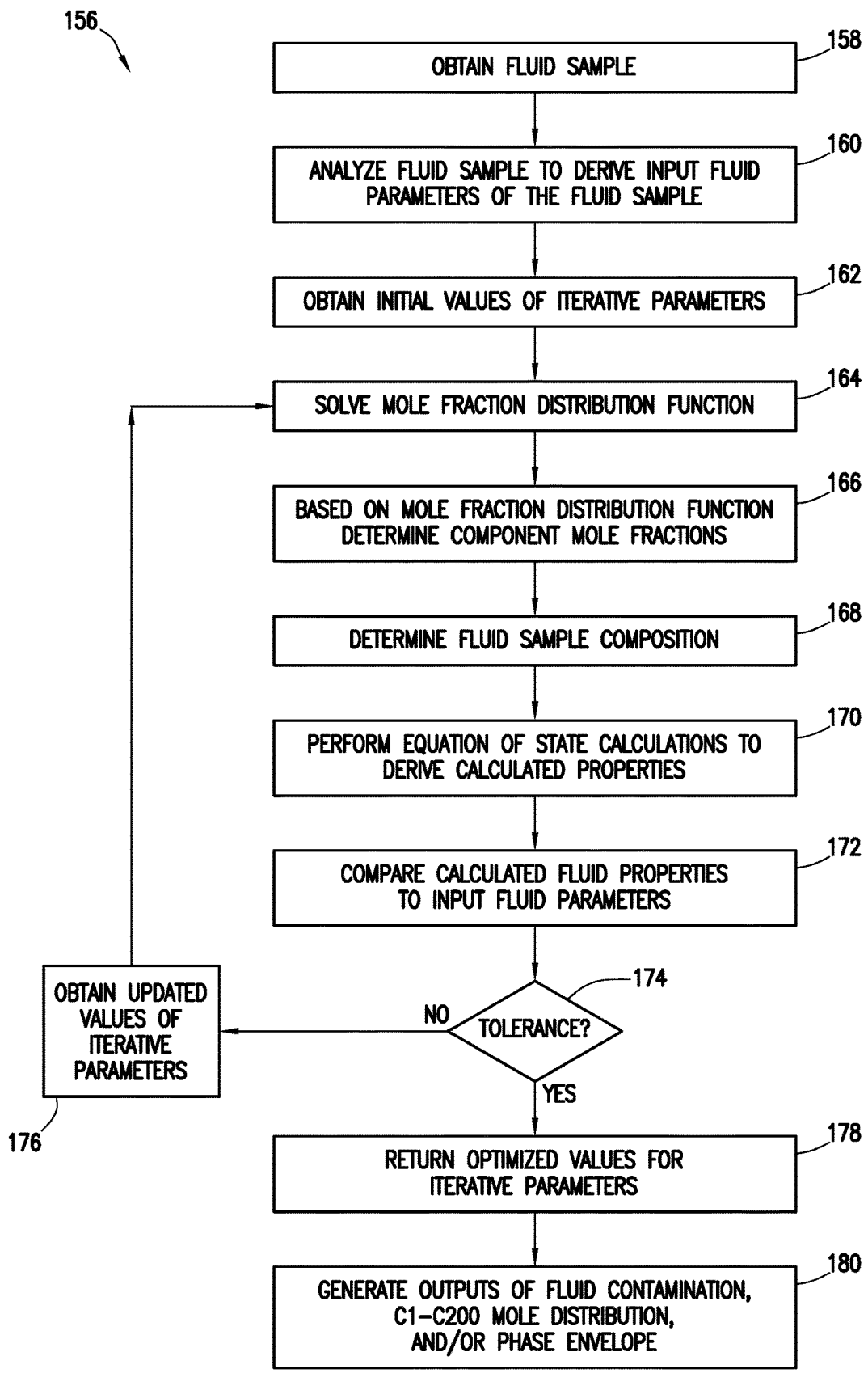
FIG. 3 is a flow chart of an example method for determining fluid contamination of a fluid sample of a reservoir fluid.

FIG. 3 shows a flow chart of an example of a method 156 for determining fluid contamination. The method 156 may be implemented using the systems implemented on FIGS. 1 and 2, for example, to determine fluid contamination (e.g., drilling fluid contamination) of a fluid sample. The method 156 may be implemented at surface 120 or in wellbore 106. By way of example, fluid analysis module 136 of downhole fluid sampling tool 100 may include a processing unit (e.g., a microprocessor, etc.) that can be operable to implement one or more of the method steps of method 156. By way of further example, information handling system 140 may also include a processing unit 142 (e.g., a microprocessor, etc.) that can be operable to implement one or more of the method steps of method 156. As will be appreciated, processing may occur either in wellbore 106, at surface 120, at a remote location, or a combination of these locations.

In step 158, a fluid sample may be obtained. The fluid sample may be a fluid sample from a reservoir of interest, for example, from subterranean formation 104 shown on FIGS. 1 and 2. Any suitable technique may be used to obtain fluid sample. As described previously, downhole fluid sampling tool 100 may be used to collect fluid sample on a drill string 102 (e.g., FIG. 1) or on a wireline 150 (e.g., FIG. 2), for example. For example, downhole fluid sampling tool 100 may be operated to obtain a fluid sample. The fluid sample may be contaminated with a well fluid, such as drilled fluid. The fluid sample may be obtained at formation temperature and pressure. It should be understood that downhole fluid sampling tool 100 is merely illustrative of one example apparatus that may be used in obtaining a fluid sample and those of ordinary skill in the art should be able to select an appropriate apparatus and associated methodology to obtain a fluid sample. The fluid sample need not necessarily be collected downhole. By way of example, the techniques described herein may be used to characterize the fluid sample of a produced fluid that may be obtained at surface 120. After fluid sample is obtained, subsequent processing steps (e.g., steps 160 to 180) may occur at surface 120 or in wellbore 106. Alternatively, fluid sample may be transferred to a remote location for one or more of the subsequent processing steps.

In step 160, the fluid sample may be analyzed to derive input parameters that characterize the fluid sample. Without limitation, the input parameters may be obtained from measurements of the fluid sample. The measurements may be performed in wellbore 106, at surface 120, or at a remote location. The downhole fluid sampling tool 100 or other suitable formation evaluation tools may be used to analyze the fluid sample. Any measuring instrument capable of producing a measurable response to the change of the fluid property may be used. The measuring instrument may contain a detector and/or sensor detecting, for example, density, resistivity/conductivity, viscosity, chromatography, radioactivity, dielectric constant, optical density, magnetic resonance, weight, acoustic impedance, acoustic velocity, optical response, diffusion coefficients, molecular weight, refractive index at various wavelengths, and combinations thereof. One or more sensors or detectors (e.g. sensor 134 of downhole sampling tool 100 shown on FIG. 1) may be used in the measuring instrument.

The input parameters of the fluid sample that may be derived may include fluid properties that may be obtained from measurements of the fluid sample, including, without limitation, one or more of component concentrations (e.g., weight %, etc.), gas-to-oil ratio, live oil density (or dead oil density) and bubble point. Additional fluid properties that may be derived may include one or more of volume fraction of water, API gravity, live oil viscosity, formation temperature, or formation pressure, among others. The component concentrations obtained from these measurements may typically be a lumped component concentration with concentration of heavier hydrocarbons lumped together. By way of example, the component concentration may be provided showing fractions of carbon dioxide ($CO_2$), methane ($CH_4$), ethane ($C_2H_6$), propane ($C_3H_8$), butane ($C_4H_{10}$), pentane ($C_5H_{12}$), and the C6+ group. The C6+ group may include the concentration of all hydrocarbons with six or more carbon atoms lumped into a single component concentration. In some instances, the C5 hydrocarbons may not be separately reported, with the C5+ hydrocarbon group lumped into a single component concentration. Moreover, some of the lower hydrocarbons, such as the C3, C4, or C5 hydrocarbons may also be grouped and reported together, for example, C3-C4 hydrocarbon group, C3-C5 hydrocarbon group, and/or C4-C5 hydrocarbon group. These concentrations may be provided as weight or mole percentages. "Live oil" typically refers to an oil at reservoir conditions. A fluid sample at reservoir conditions may be referred as "live oil." The live oil density of the fluid sample may be obtained from measurements at reservoir conditions. Without limitation, the live oil density may be obtained using a density sensor, for example, on downhole fluid sampling tool 100. The bubble point may include the temperature and pressure at which the first bubble of gas comes out of the fluid sample. Without limitation, the bubble point may be obtained either from measurement or derived from empirical correlation. Without limitation, the gas-to-oil ratio may be obtained by measuring the quantity of vapor component and liquid components of crude oil using near infrared absorption peaks. The ratio of methane to the oil peak on a single phase live crude oil may be directly related to gas-to-oil ratio.

Additional input parameters may also include mud filtrate composition. The term "mud filtrate" typically refers to the liquid part of a drilling fluid, for example, that passes through filter cake. Any suitable method may be used to derive the mud filtrate composition, including a mud log.

In step 162, initial values for iterative parameters may be determined. The iterative parameters may be determined based on one or more of the input parameters. The iterative parameters may be optimized by iteration through method 156, for example, steps 164 to 16. The iterative parameters may include one or more of molecular weight of C6+ components ($\lambda 1$), density of C36+ components ($\lambda 2$), and/or fluid contamination ($\lambda 3$). The molecular weight of C6+ components ($\lambda 1$) and density of C36+ components ($\lambda 2$) may be for a reservoir fluid that is considered clean without any contaminants. The molecular weight of C6+ components ($\lambda 1$), density of C36+ components ($\lambda 2$), and fluid contamination ($\lambda 3$) may be unknown variable whose value may be optimized using method 156. Using the optimized values, component concentrations of the reservoir fluid, including a delumped component concentration, may be determined. The initial values for molecular weight of C6+ components (λ1) and density of C36+ components (λ2), and fluid contamination (λ3) may derived using the input parameters obtained in step 160 from analysis of fluid sample.

Figure 4:
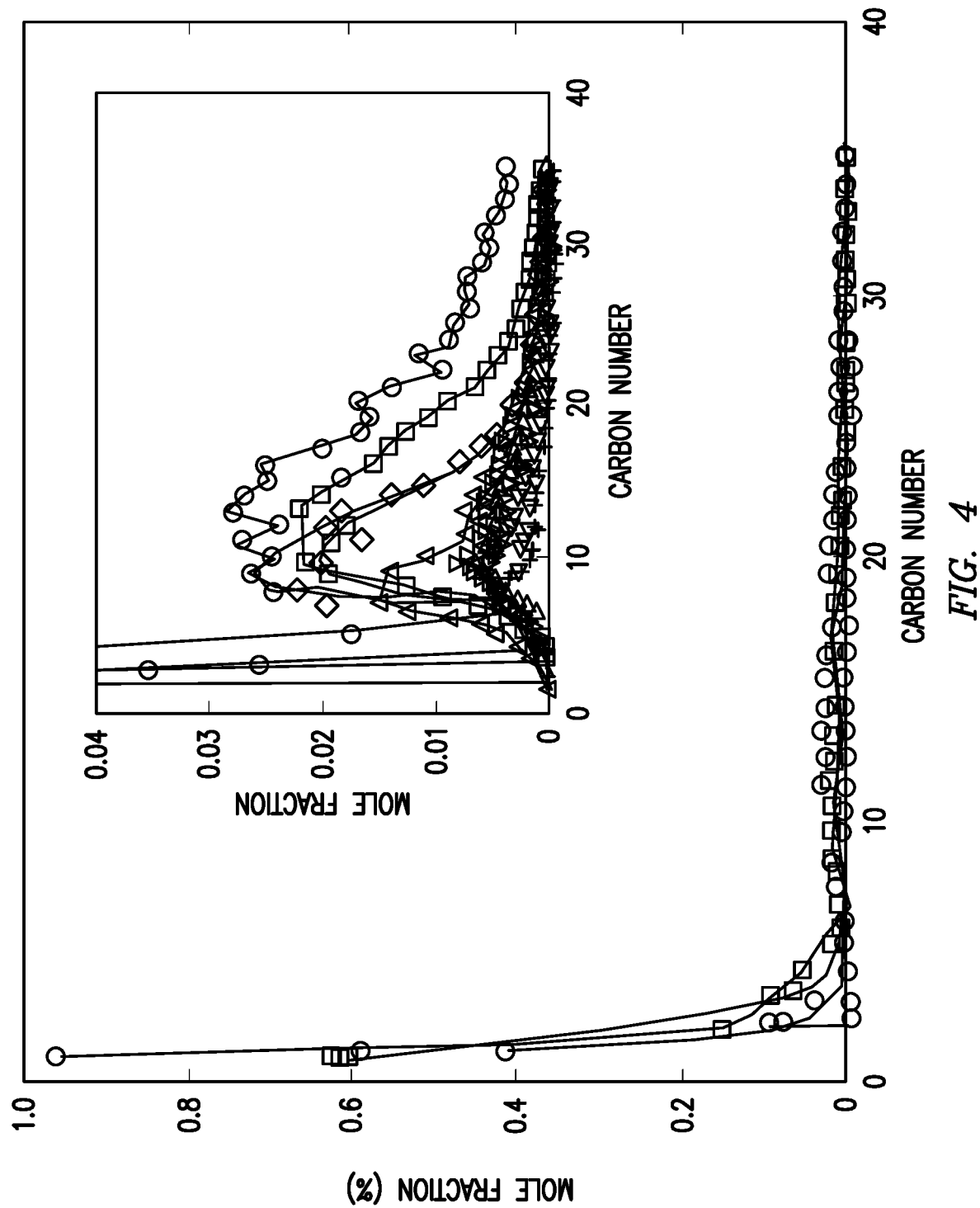
FIG. 4 is chart of single carbon number mole fraction distribution of different live oil samples, wherein the inset shows a zoomed-in view of the C5 to C36 plus components.
Figure 5:
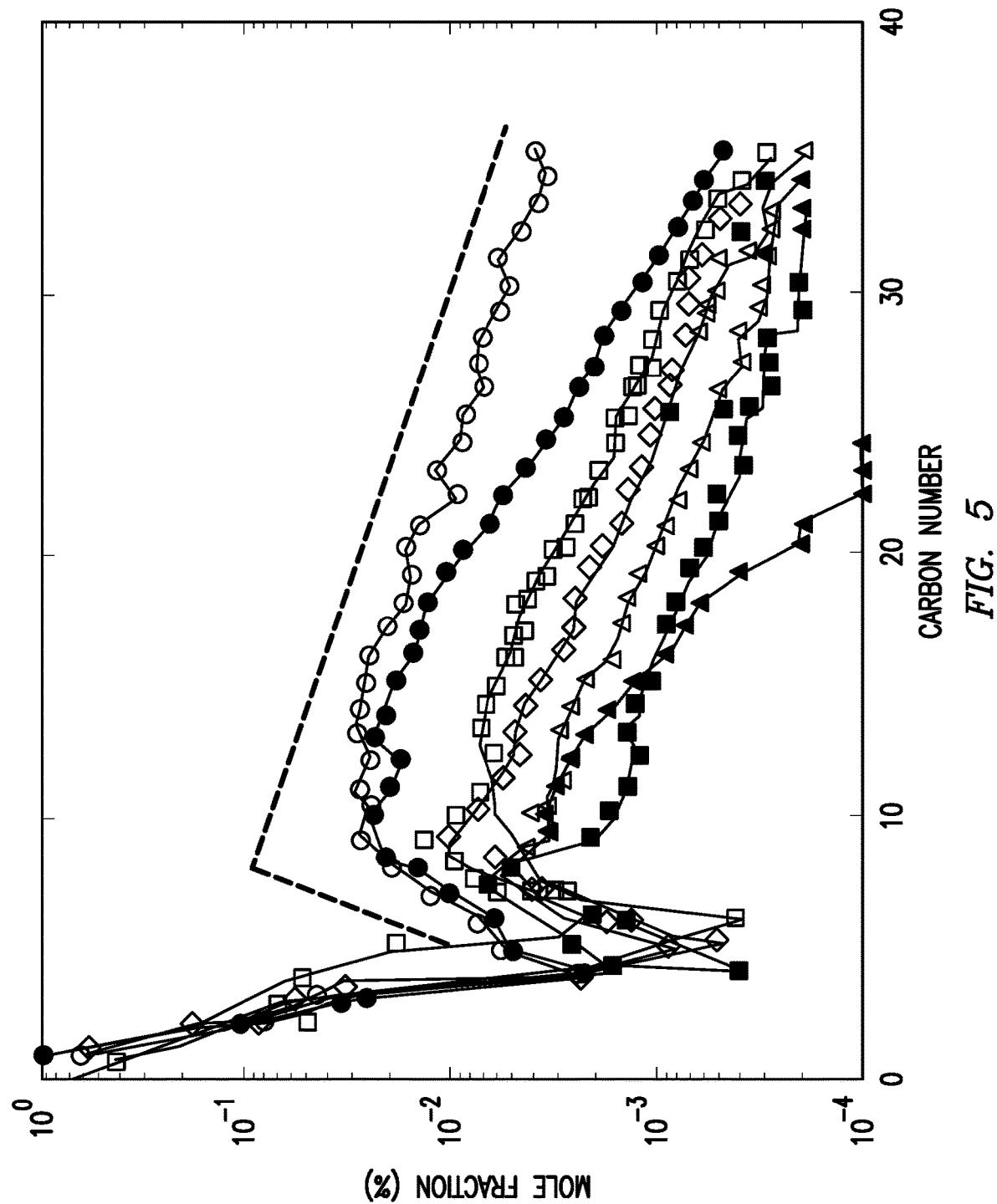
FIG. 5 is a chart of the logarithm of the single mole fraction distribution shown on FIG. 4.

Next, a mole fraction distribution function may be used to determine component mole fractions of the reservoir fluid. In step 164, the mole fraction distribution function may be solved and, in step 166, the component mole fractions of the reservoir fluid may be determined based on the mole fraction distribution function. The mole fraction distribution function may characterize reservoir fluid as a function of mole fraction of different components of the fluid. FIG. 4 shows a live oil single carbon number mole fraction distribution for a number of reservoir fluids. As illustrated, the mole fraction distribution is provided on FIG. 4 for over ten light oil/gas condensate samples based on lab gas chromatography and distillation results. As illustrated, all the samples have a maximum fraction at C1, which may be due to the nature of light oil, for example. The mole fraction then declines dramatically with increasing carbon number. However, another increase is observed at C5 until a secondary maximum may be achieved at C8. Then the mole fraction decreases towards a plateau of zero. The exponential increasing trend from C5 to C8 and exponential decreasing trend from C8 to C36+ may be observed in FIG. 5, which is a semi-log plot of FIG. 4. Based on these observations, a split exponential distribution function may be used as the mole fraction distribution function as follows:

$$z_i = \begin{cases} \sigma e^{-\tau_1(k-i)^{\alpha_1}}, & i = 5, \ldots, k \\ \sigma e^{-\tau_2(i-k)^{\alpha_2}}, & i = k, \ldots, 200 \end{cases} \quad (1)$$

In equation 1, $z_i$ is the mole fraction of component with carbon number i and k is the single carbon number with the local maximum mole fraction, which may vary for different fluid samples. For the group of reservoir fluid samples shown on FIGS. 4 and 5, k=8~13. $\sigma, \tau$, and $\alpha$ are parameters to be solved for certain samples, wherein $\sigma$ is a scaling parameter to tune a total mole fraction of C5 to C200 and $\tau$ and $\alpha$ are parameters to tune the increasing and decreasing trends (e.g., concavity of the curves). The subscripts 1 and 2 in equation 1 denote the increasing and decreasing regions, respectively. The subscript i represents the single carbon number.

In step 164, the mole fraction distribution function may be solved. The mole fraction distribution function may include one or more unknown parameters that may need to be solved to characterize the component mole fractions of a reservoir fluid. By way of example, equation 1 includes five unknown parameters ($\sigma, \tau_1, \tau_2, \alpha_1$, and $\alpha_2$) that need to be solved for before component mole fractions may be determined. One or more constraints may be used for determining the unknown parameters in the mole fraction distribution function. Five constraints may be needed for solving equation 1 as there are five unknown parameters. The basis of the constraints that may be used for the mole fraction distribution function may include, without limitation, mole balance, mass balance, the continuity nature of the functions, or combinations thereof. The constraints may also include theoretical assumptions, semi-empirical assumptions, or empirical assumptions. Thus, determining the unknown parameters may be a semi-empirical or empirical determination. Accordingly, in step 164, the mole fraction distribution function (e.g., equation 1) may be solved to determine the unknown parameters.

In step 166, the mole fraction distribution function may be used to determine component mole fractions of the reservoir fluid. The reservoir fluid may be considered a clean reservoir fluid as the component mole fractions determined in step 166 may be of the reservoir fluid without contamination. Without limitation, with the unknown parameters of the mole fraction distribution function known, the mole fraction distribution function may be used to determine the C1-C200 component. By way of example, the component mole fractions determined from the mole fraction distribution function may be a delumped component concentration that includes mole distribution of components, including for plus fractions (C5+, C6+, etc.). Where equation 1 may be used, the mole fraction or $z_i$, (i=1 to 200) of the sample fluid may be obtained.

In step 168, the composition of the fluid sample may be determined. The fluid sample composition may be component mole fraction. The composition determined in step 168 may be the composition of the fluid sample. In other words, the composition may the composition of the reservoir fluid contaminated with the well fluid (e.g., drilling fluid). In contrast, the component mole fractions determined in step 166 are for the clean reservoir fluid without contaminants. In general, the composition of the fluid sample may be determined using the component mole fractions from step 166 and the fluid contamination (λ3). By way of example, equation 2 below may be used to determine the composition of the fluid sample:

$$mi_{cont} = \frac{\lambda_3 mi_{mud} + (1-\lambda_3)mi_{clean}}{\sum_{i=1}^{200}(\lambda_3 mi_{mud} + (1-\lambda_3)mi_{clean})} \quad (2)$$

Wherein λ3 is fluid contamination, $mi_{clean}$ is the mole fraction of component i for the reservoir fluid, $mi_{mud}$ is the mole fraction of component i in the mud filtrate, and i represents the single carbon number. For example, i may be an integer from 1 to 200.

In step 170, equation of state calculations may be performed to derive calculated fluid properties. The equation of state calculations may include equation of state flash calculations carried out over the component mole fractions of the fluid sample determined in step 166. Equation of state flash calculations may be used to derive the gas to oil ratio and dead oil density, among other fluid properties, of the fluid sample. Equation of state calculations may be used to derive the phase envelope and bubble point of the fluid sample, among other properties. To reduce the computational complexity of the equation of state calculations, the component mole fractions of the fluid sample may be lumped, for example, to C1, C2, . . . , C34, C35, and C36+ mole fractions. The calculated fluid properties determined by the equation of state flash calculations may include one or more of gas-to-oil ratio, dead oil density, bubble point, and/or phase envelope, for example. "Dead oil" typically refers to an oil at sufficiently low pressure that it contains substantially no dissolved gas or relatively thick oil that has lost its volatile components. Additional calculated fluid properties may include, without limitation, liquid mole fraction distribution, vapor mole fraction distribution, the density, molecular weight and mole volume for the liquid and vapor portion of the live oil.

The equation of state calculations may be based on equation of state equations that represent the functional relationship between pressure, volume, and temperature of the fluid sample. Equations of states may be used to predict physical properties, such as macroscopic pressure-volume-temperature properties, including bubble point, dew point, phase envelope, viscosity, gas-to-oil ratio, density, combinations thereof.

Equation of state calculations may use information or properties such as temperature, pressure, and composition. For example, one simple equation of state is PV=nRT, known as the ideal gas law, where P=pressure, V=volume, n=moles, R=Ideal Gas Constant (also used for units conversion), and T=absolute temperature (Kelvin or Rankine). When the physical properties and composition of the reservoir fluid under a given set of conditions are known, the behavior of the reservoir fluid at other pressures and temperatures may be predicted. Equations of state that may be used may include, for example, expansions of the ideal gas law to account for individual molecular compositions. According to some embodiments, they are third order equations. Any of a variety of equations of state may be used. The equation of state may be cubic or non-cubic. The equation of state may vary depending on or more compositional components of the fluid sample. The equations of state have many names, as they have been modified to improve the match between predicted and observed behavior. Without limitation, the equation of state may be selected from one or more of Boyle, Van der Waals, Redlich-Kwong, Soave-Redlich-Kwong, Peng-Robinson, Peng-Robinson-Stryjek-Vera, Patek-Teja, Schm it-Wenzel, or Esmaeilzadeh-Roshanfekr.

In step 172, the calculated fluid properties may be compared to the input fluid parameters. As described above, the input fluid parameters may be derived from analysis of the fluid sample in step 160. By way of example, gas-to-oil ratio and live oil density may be measured. From the live oil density, the dead oil density may be determined. The calculated fluid properties may also include a calculated gas-to-oil ratio and a calculated dead oil density. Without limitation, this comparison may include comparing the calculated gas-to-oil ratio with the input gas-to-oil ratio obtained from fluid analysis in step 160. Without limitation, this comparison may further include comparing the calculated dead oil density, gas to oil ration and bubble point pressure with those from input data from fluid analysis in step 160.

A tolerance error may be used, step 174, to determine if another iteration through the mole fraction distribution function (steps 162-170), fluid sample composition determination (step 168), and the equation of state calculations (step 170) may be required. The tolerance error may be a small value selected to impact the iteration number and total calculation time, but should have minimal impact on the final results. Without limitation, if the relative differences between the input fluid parameters and the calculated fluid parameters are not within a tolerance error, then another iteration may be required. By way of example, if the relative difference between the calculated gas-to-oil ratio and input gas-to-oil ratio and between the calculated dead oil density and dead oil density derived from the input dead oil density, are not within a tolerance error, then another iteration may be required. If the tolerance error determines that another iteration may be required, the iterated values (e.g., molecular weight of C6+ components ($\lambda 1$), density of C36+ components ($\lambda 2$), and/or fluid contamination $\lambda 3$) may be updated (step 176) and steps 164 to 174 may be repeated. Updating values for the molecular weight of $C_{6+}$ components ($\lambda 1$), density of $C_{36+}$ components ($\lambda 2$), and/or fluid contamination ($\lambda 3$) may utilize any of a variety of different analysis algorithms, including, without limitation, Newton-Raphson method. The iteration of steps 164 to 174 may be repeated with values for the molecular weight of $C_{6+}$ components ($\lambda 1$), density of $C_{36+}$ components ($\lambda 2$), and fluid contamination ($\lambda 3$) obtained until values for the comparison of step 177 or within the tolerance error of step 174.

When the tolerance error of step 174 may be satisfied, the method 156 may move to step 178 and optimized values for iterated parameters, including the molecular weight of $C_{6+}$ components ($\lambda 1$), density of $C_{36+}$ components ($\lambda 2$), and fluid contamination ($\lambda 3$) for the reservoir fluid may be returned. In block 180, the optimized values may result in optimized values may be used to generate an output of component mole fractions (e.g., C1-C200 mole distributions) and pressure-volume-temperature properties, such as bubble point and phase envelop prediction, among others, for the reservoir fluid. Output may also include the fluid contamination, which; may include for example, the drilling fluid contamination in the fluid sample of the reservoir fluid. Without limitation, the optimized values may be used to calculate the output values for component mole fractions (e.g., C1-C200 mole distributions) and pressure-volume-temperature properties. The component mole fractions may be a delumped component mole fractions. The delumped mole fractions may comprise component mole fractions for each carbon number from C1 to C200. Alternatively, the delumped component mole fractions may be expanded, but may continue to have some of the heavier hydrocarbons lumped into a group. For example, ten, twenty, thirty, or even more component mole fractions may be provided for C5+ hydrocarbons.

Figure 6:
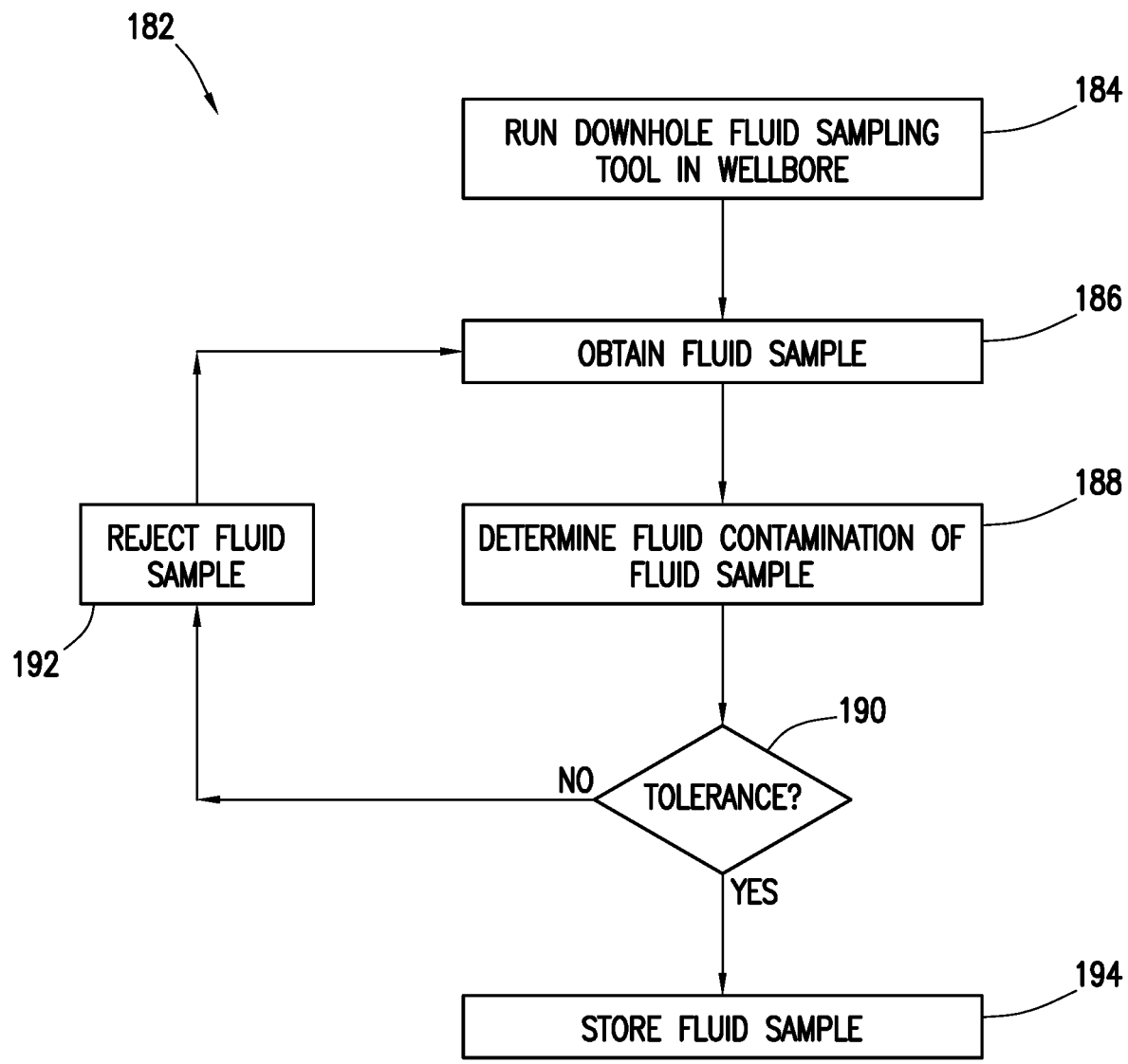
FIG. 6 is a flow chart of an example method for using a downhole fluid sampling tool to obtain and store fluid samples.

Referring now to FIG. 6, a flow chart is shown of example of a fluid sampling method 182. The fluid sampling method 182 may be implemented using the systems implemented on FIGS. 1 and 2, for example, to determine fluid contamination (e.g., drilling fluid contamination) of a fluid sample. In step 184, the fluid sampling method 182 may include running a downhole fluid sampling tool 100 in a wellbore 106, for example, as shown on FIGS. 1 and 2. The downhole fluid sample tool 100 may be run into wellbore 106 on a drill string 102 (FIG. 1), a wireline 150 (FIG. 2), or any other suitable conveyance. In the wellbore 106, the downhole fluid sample tool 100 may be used to obtain a fluid sample (step 186) from subterranean formation 104. As previously described, the fluid sample may be a fluid sample of a reservoir fluid that may be contaminated with a well fluid. For example, the reservoir fluid may be contaminated with drilling fluid. In step 188, the fluid sampling method 182 may include determining fluid contamination of the fluid sample. Determining fluid contamination may include use of a mole fraction distribution function in conjunction with an equation of state. FIG. 3 illustrates an example method 156 that determines fluid contamination of a fluid sample using a mole fraction distribution function in conjunction with an equation of state. Referring again to FIG. 6, a tolerance value may be used, step 190, to determine if the fluid sample is sufficiently free of contamination for storage in downhole fluid sampling tool 100. The tolerance value may be selected, for example, based on a number of criteria, such as industry standards. By way of example, the tolerance value may be 2% by weight or less. Without limitation, if fluid contamination of the fluid sample is above the tolerance value, then the contamination is too great, then an additional fluid sample may be needed. If the tolerance value determines that an additional fluid sample may be needed, then the fluid sample that was obtained may be rejected (step 192) and step 186 may be repeated to obtain another fluid sample.

Steps 188 and 190 may then be repeated on the newly obtained fluid sample. Without limitation, if the fluid contamination is within the tolerance value, the fluid sample may be stored (step 194). For example, the fluid sample may be stored in downhole fluid sampling tool 100 (e.g., FIGS. 1 and 2) for analysis and recovery. If desired, the method 182 may be repeated to obtain and stored additional fluid samples. Without limitation, it may be desirable to obtain and store additional fluid samples from different locations in wellbore 106.

The techniques disclosed herein for determining fluid contamination, such as method 156 and/or fluid sampling method 182, may be performed in real-time. "Real time" performance refers to "on the fly" fluid characterization accomplished during field use of downhole fluid sampling tool 100 (or other tool), as opposed to prior to the field use or post to the field use, e.g., performance in real time, such as while logging, without retrieving the downhole fluid sampling tool 100 or fluid sample from downhole. Performance of the fluid characterization in real time may allow a user to determine component mole fractions and phase envelope prediction at or about the same time as measurements are made.

Without limitation, the preceding techniques may be used in a variety of methods and systems for determining fluid contamination. Without limitation, a method for determining fluid contamination may comprise obtaining a fluid sample, wherein the fluid sample comprises a reservoir fluid contaminated with a well fluid; obtaining input parameters, wherein the input parameters comprise fluid properties obtained from measurement of the fluid sample and mud filtrate composition; obtaining initial values of iterative parameters, wherein the iterative parameters comprise fluid contamination of the fluid sample; determining component mole fractions of the reservoir fluid using the initial values of the iterative parameters in a mole fraction distribution function; determining calculated fluid properties of the reservoir fluid using equation of state flash calculating; and repeating steps of determining component mole fractions and determining calculated fluid properties and further obtaining updated values of the iterative parameters for use in the mole fraction distribution function until a comparison of one or more of the calculated fluid properties with one or more of the input parameters is within a tolerance error. Without limitation, a fluid sampling method may comprise running a downhole fluid sampling tool in a wellbore; obtaining a fluid sample of a reservoir fluid using the downhole fluid sampling tool; determining a fluid contamination of the fluid sample, wherein the determining the fluid contamination includes uses of a mole fraction distribution function in conjunction with an equation of state; and storing the fluid sample in the downhole fluid sampling tool based on the fluid contamination. Without limitation, a system for determining fluid contamination may comprise a downhole fluid sampling tool operable to obtain fluid samples of a reservoir fluid contaminated with a well fluid while the downhole fluid sampling tool is disposed in a wellbore; and a processing unit operable to (i) obtain input parameters, wherein the input parameters comprise fluid properties obtained from measurement of the fluid sample and a mud filtrate composition; (ii) obtain initial values of iterative parameters, wherein the iterative parameters comprise fluid contamination of fluid sample; (iii) determine component mole fractions of the reservoir fluid using the initial values of the iterative parameters in a mole fraction distribution function; (iv) determine calculated fluid properties of the reservoir fluid using equation of state flash calculating; and (v) repeatedly determine component mole fractions and determining calculated fluid properties and further obtain updated values of the iterative parameters for use in the mole fraction distribution function until a comparison of one or more of the calculated fluid properties with one or more of the input parameters is within a tolerance error.

These fluid characterization methods and/or systems for characterizing a fluid sample may include any of the various features of the compositions, methods, and systems disclosed herein. Without limitation, the methods and/or systems may further comprise wherein the well fluid comprises a drilling fluid. The methods and/or systems may further comprise wherein the obtaining the fluid sample comprising operating a downhole fluid sampling tool in a wellbore to obtain the fluid sample. methods and/or systems may further comprise wherein the fluid properties of the input parameters comprise a component concentration, an oil density, weight % of components, bubble point pressure and a gas-to-oil ratio. methods and/or systems may further comprise wherein the iterative parameters further comprise molecular weight of C6+ components and density of C36+ components of the reservoir fluid. The methods and/or systems may further comprise wherein the component mole fractions determined using the mole fraction distribution function are delumped component mole fractions of a lumped component concentration obtained in the step of analyzing the fluid sample. The methods and/or systems may further comprise wherein the mole fraction distribution function is represented by equation (1). The methods and/or systems may further comprise wherein the step of determining component mole fractions of the reservoir fluid comprises solving the mole fraction distribution function for one or more unknown parameters, determining the component mole fractions of the reservoir fluid based on the mole fraction distribution function; and determining a composition of the fluid sample based at least on the component mole fractions of the reservoir fluid. The methods and/or systems may further comprise wherein the comparison of one or more of the calculated fluid properties with one or more of the input parameters comprises calculated properties of gas-to-oil ratio, bubble point pressure and dead oil density with input parameters of gas-to-oil ratio, bubble point pressure and dead oil density. The methods and/or systems may further comprise wherein the downhole fluid sampling tool is run in the wellbore on a drill string. The methods and/or systems may further comprise wherein the downhole fluid sampling tool is run in the wellbore on a wireline. The methods and/or systems may further comprise wherein the fluid sample comprises a reservoir fluid contaminated with a drilling fluid. The methods and/or systems may further comprise wherein the downhole fluid sampling tool comprises an elongated tool body and a sensor. The methods and/or systems may further comprise wherein the downhole fluid sampling tool is disposed on a distal end of a drill string. The methods and/or systems may further comprise wherein the processing unit is distributed between a downhole processing unit and a processing unit disposed at a surface.

EXAMPLES

To facilitate a better understanding of the present technique, the following examples of some specific embodiments are given. In no way should the following examples be read to limit, or to define, the scope of the invention.

Figure 7:
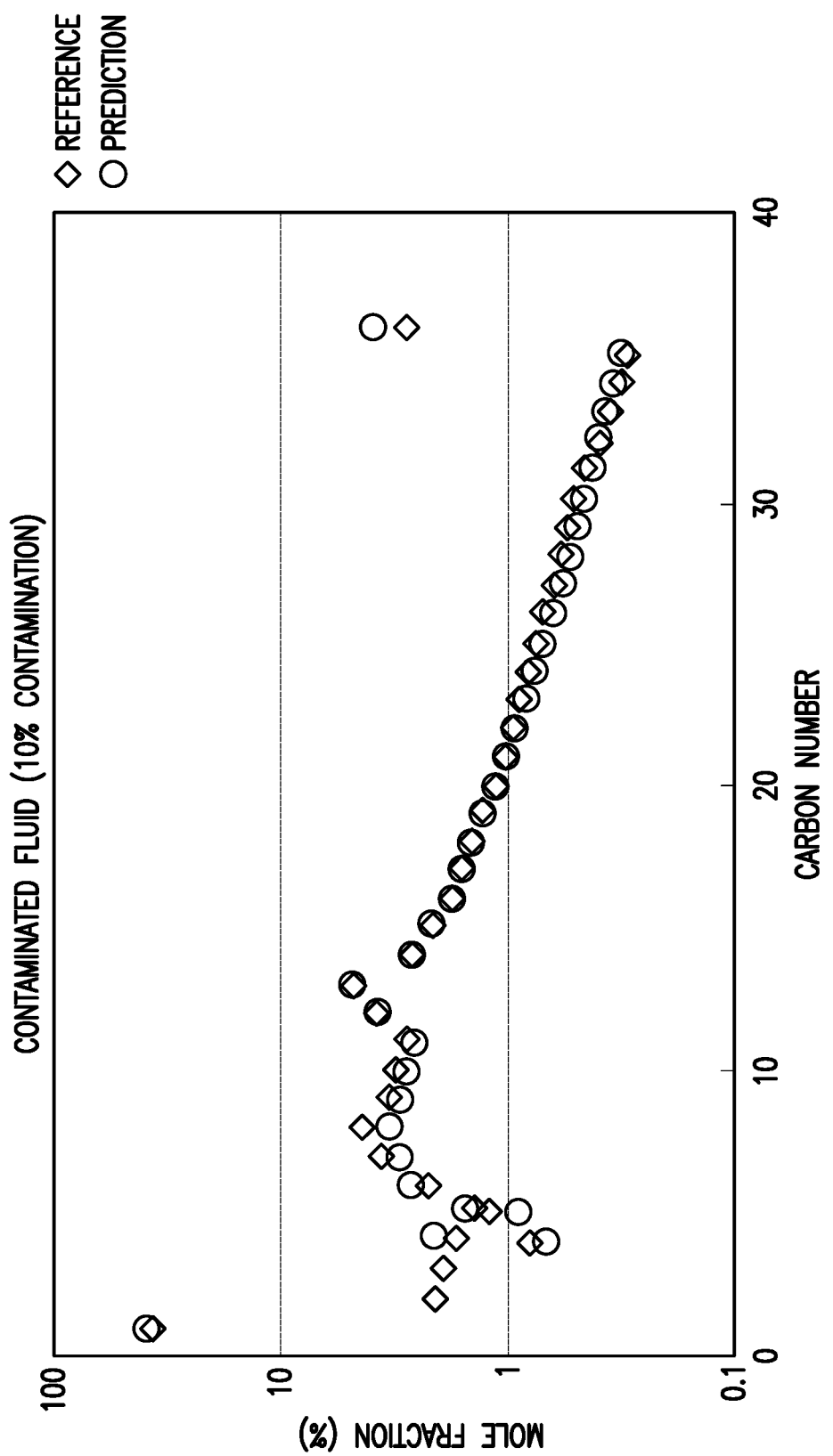
FIG. 7 is a chart that shows a comparison of predicted and gas chromatograph mole fraction distributions for a sample fluid with 10% contamination.
Figure 8:
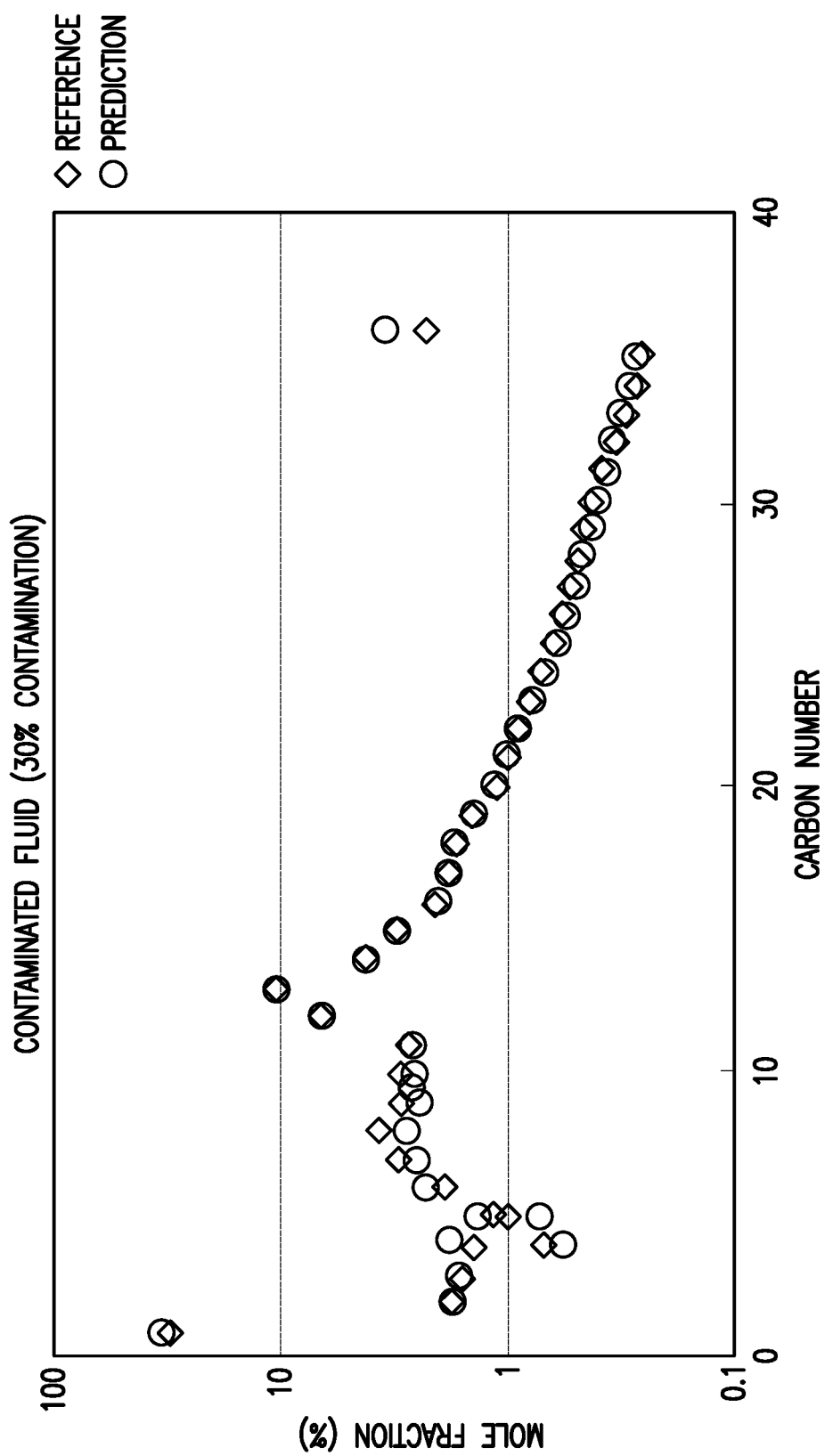
FIG. 8 is a chart that shows a comparison of predicted and gas chromatograph mole fractions for a sample fluid with 30% contamination.
Figure 9:
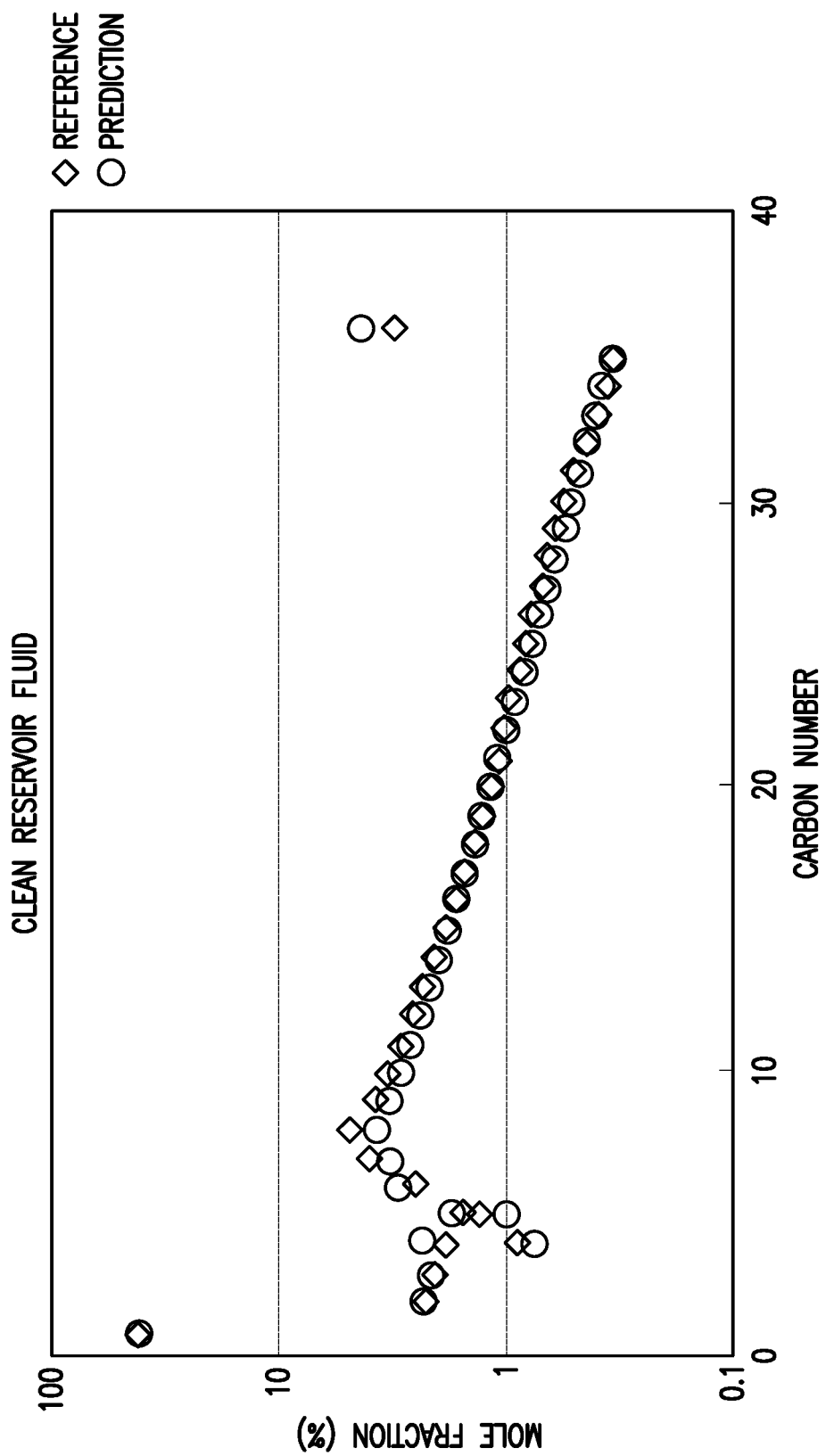
FIG. 9 is a chart that shows a comparison of predicted and gas chromatograph mole fraction distributions for a clean reservoir fluid.

Techniques disclosed herein were used to characterize two contaminated oil samples with 10% and 30% contamination by weight, respectively. The predicted component mole fractions for the contaminated oil samples from method 156 on FIG. 3 were compared with laboratory-measured gas-chromatograph data. The predicted component mole fractions for the contaminated oil samples are compared to the reference values from the gas-chromatograph data in FIGS. 7 and 8. The predicted values compare well with the reference values from the gas-chromatograph data. The predicted fluid contaminations are 10.12% and 28.95% for each sample, which illustrates that the fluid contamination may be predicted with a small bias using the routines disclosed herein. With the fluid contamination determined, the component mole fractions for the reservoir fluid may be determined. The predicted component mole fractions for the reservoir fluid are compared to the reference values from the gas-chromatograph in FIG. 9. Furthermore, the predicted component mole fractions may be used to calculate the phase envelope and bubble point pressure (Pb). The predicted phase envelope results are compared to the reference values in FIG. 10. As illustrated, there is good agreement between the predicted and reference values for phase envelope, particularly at reservoir temperatures of 150° F. and 250° F., the relative error of bubble point pressure is within 1%.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

It should be understood that the compositions and methods are described in terms of "comprising," "containing," or "including" various components or steps, the compositions and methods can also "consist essentially of or" consist of the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method for determining fluid contamination, comprising:

obtaining a fluid sample, wherein the fluid sample comprises a reservoir fluid contaminated with a well fluid;

obtaining input parameters, wherein the input parameters comprise fluid properties obtained from measurement of the fluid sample and mud filtrate composition;

obtaining initial values of iterative parameters, wherein the iterative parameters comprise fluid contamination of the fluid sample; determining component mole fractions of the reservoir fluid using the initial values of the iterative parameters in a mole fraction distribution function;

determining calculated fluid properties of the reservoir fluid using equation of state flash calculating; and repeating steps of determining component mole fractions and determining calculated fluid properties and further obtaining updated values of the iterative parameters for use in the mole fraction distribution function until a comparison of one or more of the calculated fluid properties with one or more of the input parameters is within a tolerance error.

2. The method of claim 1, wherein the well fluid comprises a drilling fluid.

3. The method of claim 1, wherein obtaining the fluid sample comprising operating a downhole fluid sampling tool in a wellbore to obtain the fluid sample.

4. The method of claim 1, wherein the fluid properties of the input parameters comprise a component concentration, an oil density, weight % of components, bubble point pressure and a gas-to-oil ratio.

5. The method of claim 1, wherein the iterative parameters further comprise molecular weight of C6+ components and density of C36+ components of the reservoir fluid.

6. The method of claim 1, wherein the component mole fractions determined using the mole fraction distribution function are delumped component mole fractions of a lumped component concentration obtained in the step of analyzing the fluid sample.

7. The method of claim 1, wherein the mole fraction distribution function is represented by the following equation:

$$z_i = \begin{cases} \sigma e^{-\tau_1 (k-i)^{\alpha_1}}, & i = 5, \ldots, k \\ \sigma e^{-\tau_2 (i-k)^{\alpha_2}}, & i = k, \ldots, 200 \end{cases}$$

wherein i is single carbon number, z is mole fraction of component with single carbon number i, k is single carbon number with local maximum mole fraction, and $\sigma_1$, $\sigma_2$, $\tau_1$, $\tau_2$, and $\alpha$ are unknown parameters to be solved.

8. The method of claim 1, wherein the step of determining component mole fractions of the reservoir fluid comprises solving the mole fraction distribution function for one or more unknown parameters, determining the component mole fractions of the reservoir fluid based on the mole fraction distribution function; and determining a composition of the fluid sample based at least on the component mole fractions of the reservoir fluid.

9. The method of claim 1, wherein the comparison of one or more of the calculated fluid properties with one or more of the input parameters comprises calculated properties of gas-to-oil ratio, bubble point pressure and dead oil density with input parameters of gas-to-oil ratio, bubble point pressure and dead oil density.

10. A system for determining fluid contamination, comprising:

a downhole fluid sampling tool operable to obtain fluid samples of a reservoir fluid contaminated with a well fluid while the downhole fluid sampling tool is disposed in a wellbore; and a processing unit operable to (i) obtain input parameters, wherein the input parameters comprise fluid properties obtained from measurement of the fluid sample and a mud filtrate composition; (ii) obtain initial values of iterative parameters, wherein the iterative parameters comprise fluid contamination of fluid sample; (iii) determine component mole fractions of the reservoir fluid using the initial values of the iterative parameters in a mole fraction distribution function; (iv) determine calculated fluid properties of the reservoir fluid using equation of state flash calculating; and (v) repeatedly determine component mole fractions and determining calculated fluid properties and further obtain updated values of the iterative parameters for use in the mole fraction distribution function until a comparison of one or more of the calculated fluid properties with one or more of the input parameters is within a tolerance error.

11. The system of claim 10, wherein the downhole fluid sampling tool comprises an elongated tool body and a sensor.

12. The system of claim 10, wherein the downhole fluid sampling tool is disposed on a distal end of a drill string.

13. The system of claim 10, wherein the processing unit is distributed between a downhole processing unit and a processing unit disposed at a surface.

14. The system of claim 10, wherein the fluid properties of the input parameters comprise a component concentration, an oil density, bubble point pressure and a gas-to-oil ratio, and wherein the component concentration is a lumped component concentration.

15. The system of claim 10, wherein the iterative parameters further comprise for molecular weight of C6+ components and density of C36+ components of the reservoir fluid.

* * * * *